(12) United States Patent
Tribe (10) Patent No.: US 7,804,069 B2
(45) Date of Patent: Sep. 28, 2010

(54) IMAGING APPARATUS AND METHOD (75) Inventor: William R. Tribe, Cambridgeshire (GB)

(73) Assignee: TeraView Limited, Cambridge (GB)

( * ) Notice: Subject to any disclaimer, the term of this patent is extended or adjusted under 35 U.S.C. 154(b) by 0 days.

(21) Appl. No.: 11/228,353

(22) Filed: Sep. 19, 2005

(65) Prior Publication Data
US 2006/0113480 A1 Jun. 1, 2006

(30) Foreign Application Priority Data
Sep. 17, 2004 (GB) ................................. 0420748.6

(51) Int. Cl.
G01J 1/10 (2006.01)
G01J 3/00 (2006.01)
(52) U.S. Cl. .................. 250/341.1; 250/341.8; 250/340
(58) Field of Classification Search ............. 250/495.1, 250/358.1, 341.1, 341.2, 339.02, 339.06, 250/339.12, 370.08, 330, 340, 341.8
See application file for complete search history.

(56) References Cited

U.S. PATENT DOCUMENTS 6,865,014 B2* 3/2005 Ciesla et al. ................ 359/326

2003/0149346 A1* 8/2003 Arnone et al. .............. 600/309
2003/0178584 A1* 9/2003 Arnone et al. ............ 250/495.1
2004/0130725 A1* 7/2004 Kido et al. .................. 356/484

FOREIGN PATENT DOCUMENTS

| GB | 2 359 716 | 8/2001 |
| GB | 2 360 186 | 9/2001 |
| GB | 2397207 A | 7/2004 |
| WO | WO 01/48457 | * 5/2001 |

* cited by examiner

Primary Examiner—David P Porta
Assistant Examiner—Yara B Green
(74) Attorney, Agent, or Firm—Dickstein Shapiro LLP (57) ABSTRACT A method for imaging a sample, the method comprising the steps of: (a) irradiating the surface of a sample with a source of coherent substantially continuous radiation with a frequency in the range 25 GHz to 100 THz; (b) detecting said radiation reflected from or transmitted by the sample; (c) providing and detecting a probe beam having a phase related to that of the radiation leaving the source; (d) analysing the detected radiation for at least one characteristic feature within the radiation and monitoring any change in phase of such at least one feature in order to derive structural information about the sample as a function of depth from the surface of the sample.

15 Claims, 11 Drawing Sheets

IMAGING APPARATUS AND METHOD

The present invention relates to the field of imaging apparatus and methods. More specifically, the present invention relates to imaging using frequencies in the range overlapping the infrared and microwave parts of the spectrum. This frequency range encompasses the so-called Terahertz (THz) frequency range and is often referred to as Terahertz radiation.

Recently, there has been considerable interest in THz pulse imaging (TPI) which is showing promising results for both medical and non-medical use. THz radiation is non ionising radiation. Therefore, it is believed to be medically safer than well established x-ray techniques. The lower power levels used (nW to µW) also suggest that heating effects are not problematic, as may be the case with microwaves for example.

THz pulse imaging uses a plurality of frequencies within a single pulse in order to probe the frequency dependent absorption characteristics of the sample under test. Pulsed sources suffer from the drawback that they are expensive and also it is difficult to efficiently transmit pulses down optical waveguides etc. The complexity of the transmitted and reflected pulses, in lossless and in particular lossy mediums, also renders interpretation of the pulsed data difficult.

THz continuous wave imaging systems are known, see for example GB2359716, but such systems are unable to probe the internal structure of an object.

The present invention addresses the above problems and, in a first aspect, provides a method for imaging a sample, the method comprising the steps of:
  a) irradiating the surface of a sample with a source of coherent substantially continuous radiation with a frequency in the range 25 GHz to 100 THz
  b) detecting said radiation reflected from or transmitted by the sample
  c) providing and detecting a probe beam having a phase related to that of the radiation leaving the source
  d) analysing the detected radiation for at least one characteristic feature within the radiation and monitoring any change in phase of such at least one feature in order to derive structural information about the sample as a function of depth from the surface of the sample.

It should be noted that an interrupted beam (i.e. sequentially on-off) is to be considered "continuous" wave (CW) radiation if the frequency content is substantially monochromatic, but pulsed if it substantially broadband. CW radiation would still result if the beam was on for only 1/10000 of the time it was off (this is termed a low duty cycle); the "on" beam will still complete many oscillatory cycles during the on period.

Therefore the term substantially continuous is hereinafter taken to mean that the radiation source, when in the on-condition, completes several complete oscillatory cycles, so that the frequency content is not substantially altered, from that of true CW, by the on/off switching cycle.

At least one characteristic feature in the radiation is measured. This can either be by a direct measurement of the phase itself, or by measurement of the electric field which is transmitted through or reflected from the sample, the amplitude of which will be phase dependent etc. The characteristic feature can be inherent within the radiation or it can be artificially imposed.

In order for the detecting means to be able to detect an absolute change in phase of the characteristic features with respect to the radiation which irradiates the sample, the detecting means needs to have some way of knowing information about the phase of the radiation which irradiates the sample. This can be achieved by providing and detecting a probe beam which has a known phase related to that of the radiation which is used to irradiate the sample.

The present invention exploits the knowledge that as the irradiating beam interacts with the sample the path length will change. In other words, the radiation will be retarded by the sample. This will result in the position of the at least one characteristic feature shifting with measured path length. Measuring the position of one of these features will therefore yield depth information relating to the sample. For multiple reflected/transmitted signals from the sample there will be a series of detected signals and the position of each feature will provide relative depth information about the sample.

The method can further comprise the step of obtaining a reference signal. This reference signal is preferably taken without the presence of the sample and for reflection sensitive system configurations is preferably obtained by reflecting the radiation off a mirror which is substantially perfectly reflecting. The at least one characteristic feature within the radiation upon interaction with the sample can then be compared to the equivalent at least one characteristic feature in the reference signal in order to determine any change in phase.

Alternatively, where the detected radiation comprises multiple reflected or transmitted signals from the sample, the method further comprises determining the at least one characteristic feature within the radiation for each of the multiple signals and comparing such features in order to determine any changes in phase.

Conveniently standard data processing techniques are used to de-convolve a detected signal into its various components.

Preferably, the present invention exploits features that are inherent within the radiation and uses these as the characteristic features. This can be achieved by exploiting a feature inherent in coherent radiation sources, namely the coherence length of the source. If the sample were to be replaced with a perfectly reflecting mirror, for example, then for a perfect coherent source the detected radiation would be perfectly sinusoidal in form.

However, all coherent radiation sources contain irregularities such that over sufficient lengths they lose coherence. Such an effect is visible if a laser beam is split into two parts in a Michelson interferometer and then re-combined to produce an interference pattern. If the path lengths travelled in the two arms of the interferometer are equal then the fringe visibility will be at a maximum. As the path length of one path is then changed then the visibility will decrease. For practical purposes the coherence length is usually defined as the path length difference that corresponds to a fringe visibility of 50%.

A more mathematical definition that is often used equates the coherence length to the speed of light divided by the linewidth of the laser light. For common lasers the coherence length can range from tens of centimeters to tens of meters.

The coherence effect described above has the effect that the form of the detected waveform is modified from the perfect sinusoidal form such that the detected peak amplitude at each successive cycle decreases with increasing path length. Furthermore, the detected amplitude of the waveform will be at a maximum when the path length of the irradiating radiation from the source via the sample to the detecting means is equal to the path length of the probe beam from the source to the detecting means.

As a result of the coherence effect it is possible to identify unique features in the radiation and use these as the characteristic features that are monitored. As before, measuring the position of one of these features will therefore yield depth information relating to the sample. For multiple reflected/ transmitted signals from the sample there will be a series of detected signals and the position of each feature will provide relative depth information about the sample.

Conveniently the signal can be measured with respect to path length by providing for an optical path length in the probe beam that can be varied.

Preferably the at least one characteristic feature that is measured will be the maximum detected amplitude of the radiation. However, other phase dependent features could be measured in order to determine the depth information.

As described above it is not unusual for a coherent light source to have a coherence length in the tens of metres. In this instance the decrease in the peak amplitude between successive cycles of detected radiation will be small and may be less than the measured signal to noise ratio. Therefore preferably the radiation irradiating the sample comprises two or more frequencies in the range 25 GHz to 100 THz such that the resultant amplitude variation of the irradiating radiation is a combination of the two or more frequencies. Such an irradiating radiation waveform will exhibit more pronounced amplitude variations (compared to a single irradiating frequency) thereby allowing easier identification of the phase dependent features.

In the instance that two or more frequencies of irradiating radiation are used then preferably some or all of these frequencies will have different amplitudes to one another. This further helps in identification of the phase dependent features.

It is difficult to produce an efficient and powerful source for THz radiation as there is no good naturally occurring source of such radiation. Previously, there have been two main methods for generating THz radiation. The first has been to use a solid state radiation source such as a Gunn diode, molecular laser, free electron laser, cascade laser etc. The second has been to convert commonly available radiation such as radiation in the visible or near IR range, lower frequency microwaves into THz regime using a frequency conversion member.

The frequency conversion member could be an optically non-linear material which is configured to emit a beam of emitted radiation in response to irradiation by two input beams, or a photoconductive antenna which upon application of an electric field is configured to emit a beam of emitted radiation in response to irradiation by two input beams. The emitted beam has a frequency which is equal to the difference of the two input beams. In these examples, the input beams will generally have a frequency which is in the visible or near IR frequency range.

Conveniently, two beams of input radiation can be supplied by two continuous wave (CW) sources. Such continuous wave sources may be two near-infrared/visible lasers. Alternatively, a single source running in multi mode, i.e. outputting two wavelengths at the same time, could also be used.

Conveniently, the continuous wave sources are diode lasers. Diode lasers often lase at multiple frequencies simultaneously. They can therefore easily provide a way of supplying multiple frequencies of radiation simultaneously in order to produce an irradiating beam that comprises at least two frequency components. Diode lasers are also convenient to use since they are low cost units compared to other more commonly used types of lasers in imaging systems such as Ti:Sapphire lasers.

Alternatively, the optically non-linear member could be configured to emit a beam of emitted radiation in response to irradiation by an input beam, the emitted radiation having a frequency which is a harmonic of the frequency of the input radiation. The input beam could have a frequency in the low frequency microwave range.

The probe beam could be obtained by splitting the one or more of the input beams or it could be provided by splitting the Terahertz beam used to irradiate the sample. The detector could directly detect the probe beam or the probe beam could be combined with the radiation which has been transmitted through or reflected from the sample before detection. This combining of the two beams could be achieved by using a mixing component.

Once the THz is emitted from the sample, detection is required. A particularly useful detection technique is to use Electro-Optic Sampling (EOS) which uses the AC Pockels effect. The detector may comprise a photoconductive antenna.

In practice the detected radiation is likely to comprise a number of different signals reflected by or transmitted from the sample. Therefore, conveniently standard data processing techniques are used to de-convolve the detected signal into its various components.

In a further aspect of the present invention there is provided an apparatus for imaging a sample, the apparatus comprising
a source for irradiating a sample with a beam of coherent substantially continuous radiation having a frequency in the range 25 GHz to 100 THz
a detector for detecting radiation reflected from or transmitted by the sample
a probe beam having a phase related to that of the radiation leaving the source for detection by the detector
and means for analysing the detected radiation for at least one characteristic feature in the radiation and monitoring such at least one feature for any change in phase in order to derive structural information about the sample as a function of depth from the surface of the sample.

The apparatus is used to image an area of the sample. An area of the sample can be imaged in a number of different ways. For example, the sample can be moved with respect to the beam or the beam with respect to the sample. Alternatively, the sample could be illuminated with a wide beam or a plurality of beams from different sources. The detector could also be configured in a similar manner. The detector could comprises a CCD camera which will allow a large area of the sample to be examined at once.

The present invention will now be described with reference to the following non-limiting preferred embodiments in which.

Figure 1:
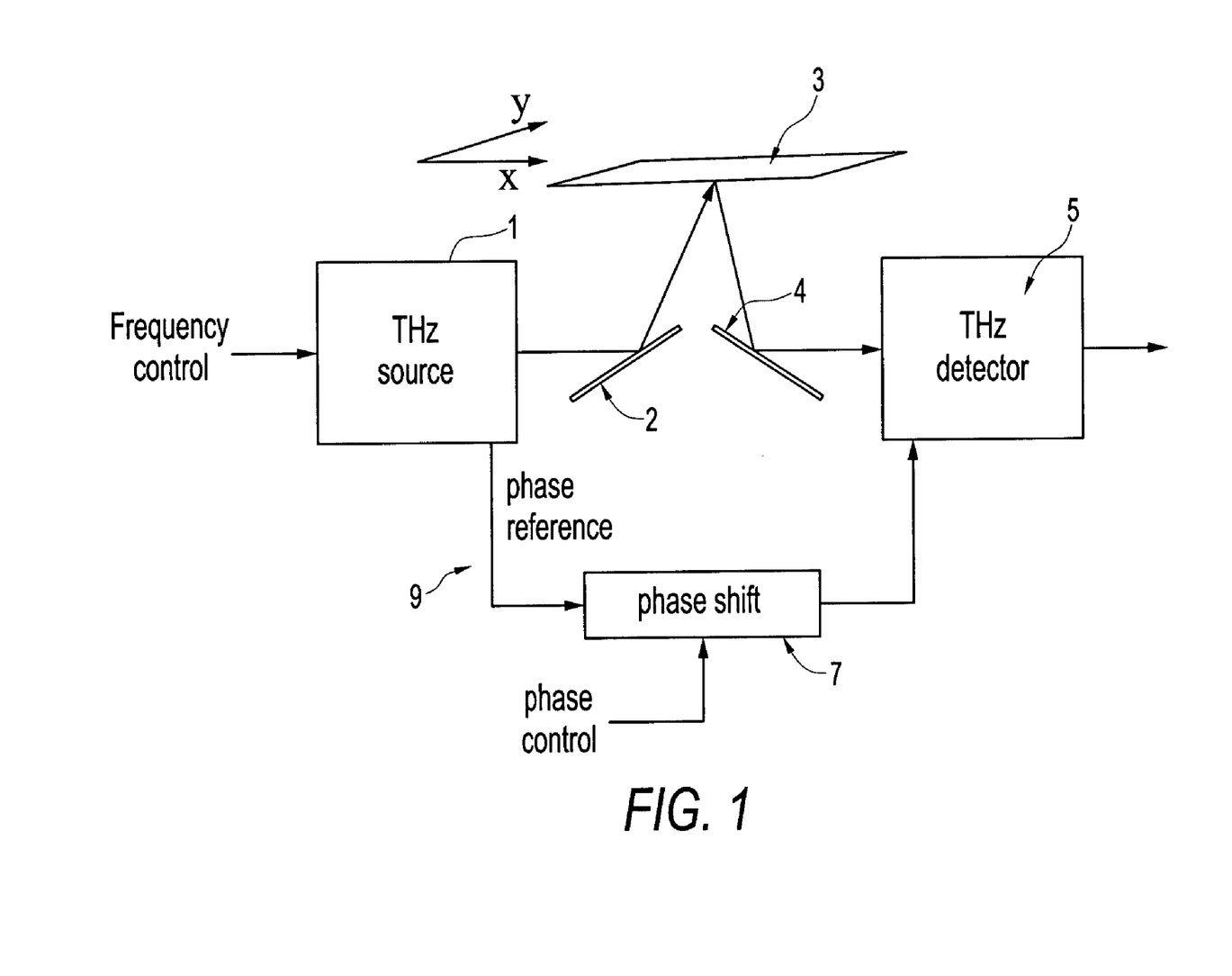
FIG. 1 shows a schematic of a generic imaging system in accordance with an embodiment of the present invention.

In the imaging system of FIG. 1, radiation is generated from THz generator 1. THz generator 1, generates terahertz radiation with a single frequency in the range from 0.025 THz to 100 THz. The THz radiation emitted from the generator 1 is reflected from mirror 2 and irradiates sample 3.

Sample 3 is located on a stage (not shown), the stage is capable of moving sample 3 through the beam of radiation emitted from generator 1 in the x and y directions. The x and y directions being taken as two orthogonal directions which are substantially perpendicular to the path of the incident irradiating radiation from the source 1.

Sample 3 will both transmit and reflect radiation. In the specific example of FIG. 1, the sample is only shown to reflect radiation and only reflected radiation will be detected. However, transmission measurements are possible although reflection measurements are preferable for depth profiling.

The reflected radiation is detected by detector 5 via mirror 4.

The detector 5 is used to detect both the amplitude and phase of the radiation emitted from the sample 3. In order to do this, there is a phase coupling/control means 7 provided between the detector (or an input to the detector) and the generator 1 or an input/output from generator 1. This phase control/coupling means will either provide the detector with a parameter corresponding to a phase input which can be varied relative to the source beam or it will vary the phase of the source beam with respect to a probe beam which will be supplied to an input of the detector.

Typically, a beam, a 'probe beam' 9 with a known phase relationship to that of the imaging radiation is fed into the phase coupling/control means 7. The phase coupling control means will typically comprise a variable optical path line which will allow the path length of the probe beam to be varied.

In many cases, the probe beam will be combined with the THz radiation which is transmitted through the sample 3. One particularly popular way is to use electro-optic sampling (EOS), a detailed explanation of which is contained in Applicant's patent/application) GB2359716.

The detection method in this generalised system configuration is such that when the THz beam arrives at the detector in phase with the THz probe beam there is a maximum in the detected signal. Hence, by altering the time delay through the phase coupling control means the beams are moved in and out of phase and an oscillatory signal with the THz time period is detected.

By moving the sample through the THz beam, or alternatively scanning the beam across the sample, it is possible to build up refractive index and depth information for the object.

Figure 2:
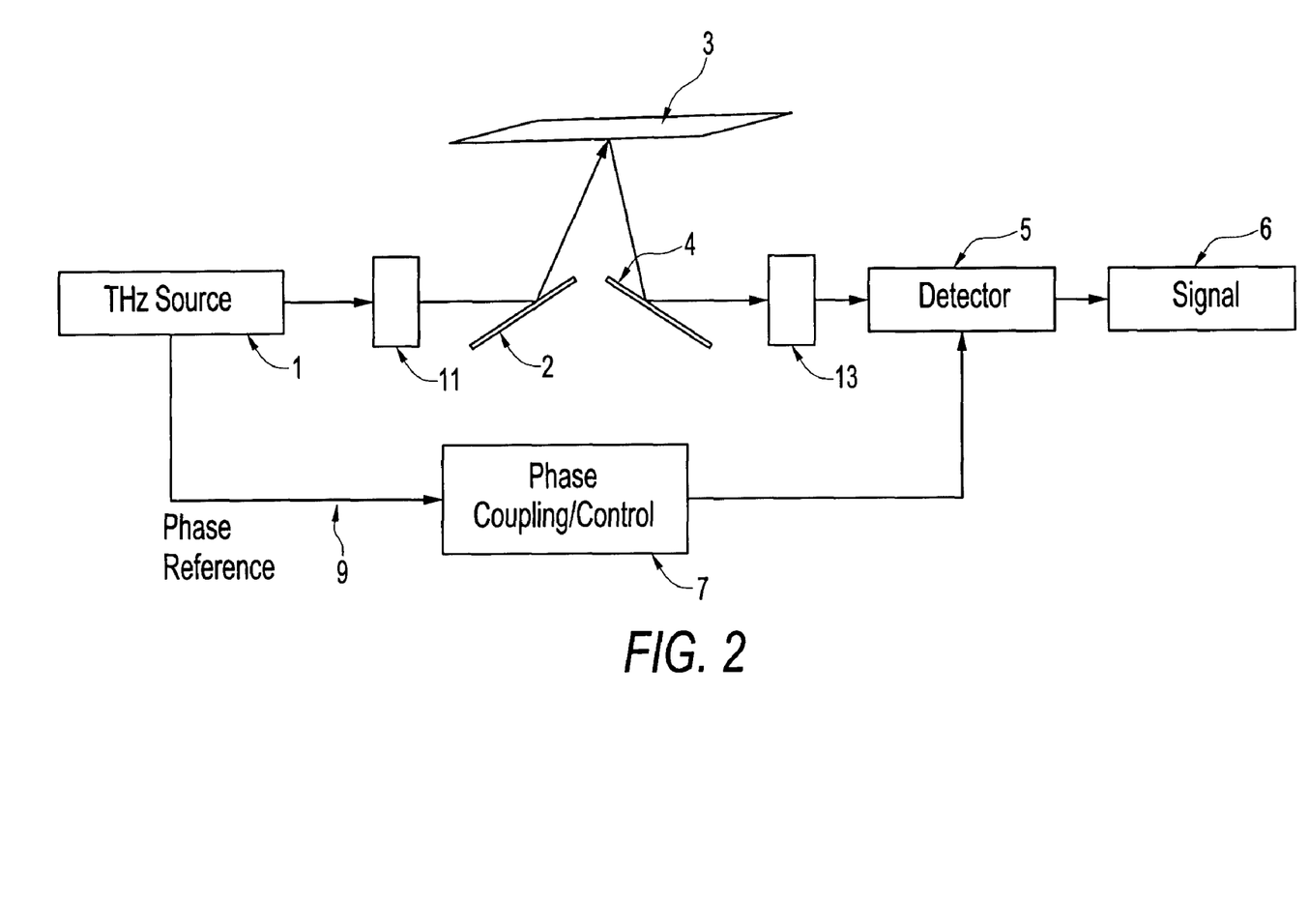
FIG. 2 shows a schematic of an alternative generic imaging system.

FIG. 2 shows a further variation on the imaging system of FIG. 1 (To avoid unnecessary repetition, like features will be denoted with like numerals). As for FIG. 1, the imaging system comprises a generator 1 which irradiates a sample 3. Radiation which is transmitted or reflected by the sample 3 is then detected by detector 5, to output signal 6. The detector 5 is configured to be able to detect a phase dependent quantity of the detected radiation via phase coupling/control means 7 which serves to input a signal into the detector concerning the phase of the radiation emitted from the generator.

In this example, the sample 3 remains fixed and the incident radiation beam is swept in the x and y direction with respect to the sample. A beam sweeping stage 11 is positioned between the generator 1 and the sample 3, this serves to 'raster' the incident radiation across the surface of the sample. A beam detection stage 13 is located between the sample 3 and the detector 5. The beam detection stages sweeps detection optics used to detect radiation transmitted through the sample 3 with the beam irradiating the sample 3. Usually, the beam sweeping stage 11 and the beam detection stage 13 will be swept together using the same stepper motor to ensure that both stages move together. In some instances such as if the detector is based on CCD or Terahertz imaging arrays of mixers, it may not be necessary to have stage 13.

Figure 3:
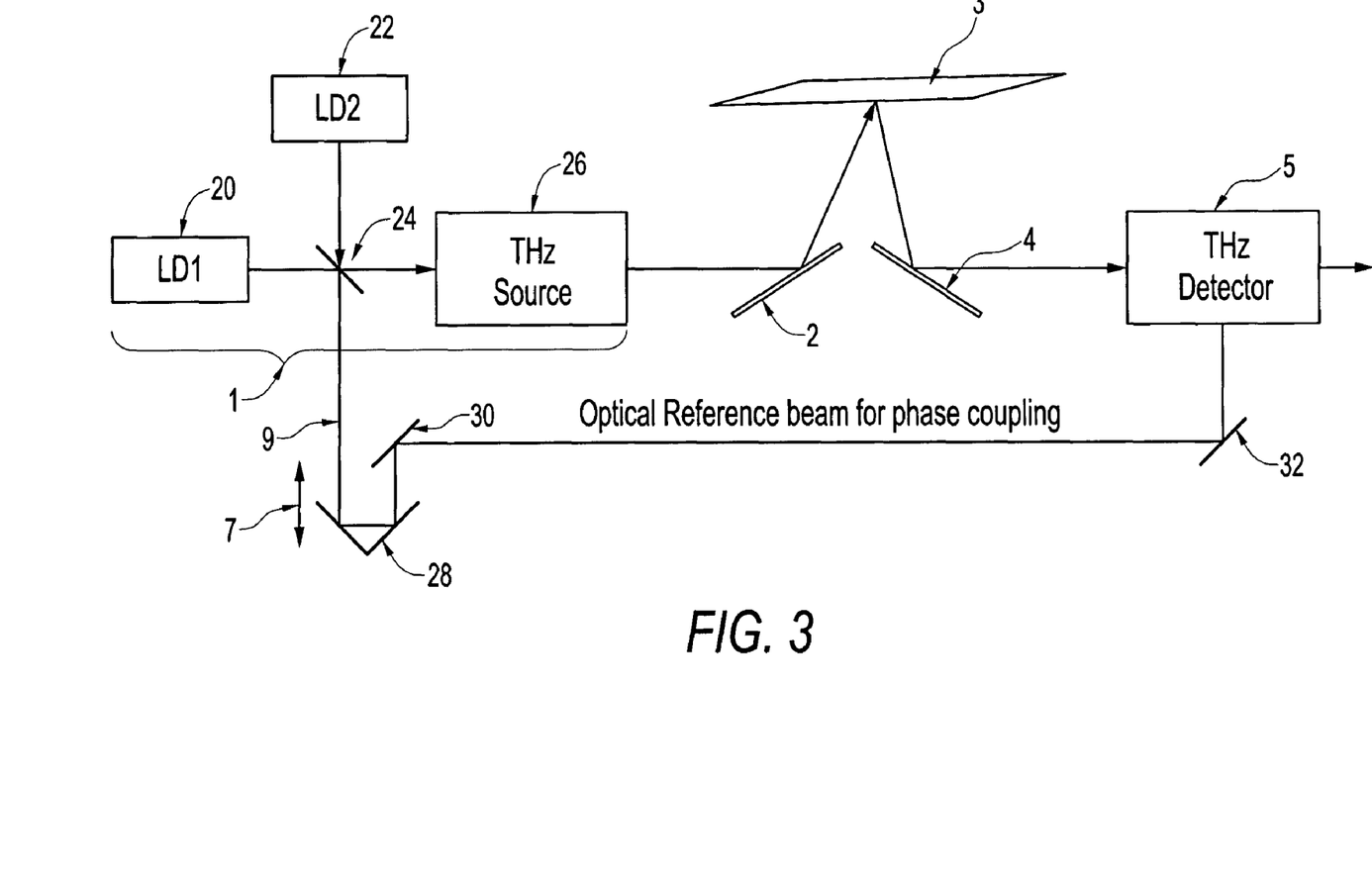
FIGS. 3 and 4 show specific configurations of imaging systems in accordance with the present invention.

FIG. 3 shows a variation on the imaging system of FIGS. 1 and 2. To avoid unnecessary repetition, like reference numerals will be used to denote like features.

The THz generator 1 comprises two laser diodes 20, 22 which are configured to emit radiation with frequencies $\omega_1$, and $\omega_2$ respectively. The radiation emitted from both laser diodes 20 and 22 is combined using beam splitter/combiner 24. The combined radiation which contains both frequencies $\omega_1$ and $\omega_2$ is then directed into THz source 26 for emitting THz radiation. The THz radiation is produced with a frequency of $\omega_1$-$\omega_2$ and THz source 26 can use the difference frequency generation methods described earlier.

The beams emitted from laser diodes 20, 22 are taken as the probe beam 9 using beam splitter 24. This probe beam will be used to give the detector information about the phase of the radiation which is emitted from the THz source 1. The probe beam is fed into optical delay line 28 which is used as the phase coupling/control means 7 explained with reference to FIG. 1.

In the optical delay line, the probe beam 9 is reflected off cube mirror 28 which is used to reflect the light through 180° and onto mirror 30 which in turn reflects the probe beam 9 into the detector 5 via the mirror 32.

Cube mirror 28 is moveable such that the path length of the probe beam can be varied as described with reference to FIG. 1. The probe beam is then directed into THz detector 5.

The sample and imaging apparatus 3 are configured such that either the sample can be moved with respect to the beam or the beam can be moved with respect to a stationary sample or both.

Improvements in the signal to noise ratio and hence acquisition times can be made by various modulation schemes. For example, dithering or oscillating of the mirror 28 will cause sinusoidal variations in the $d_p$ that can be detected using standard lock-in techniques. This is essentially a frequency modulation of the THz waveform as it is plotted out versus $d_p$. Similarly, it is possible to modulate the amplitude or frequencies of the sources outputting the radiation $\omega_1$ and $\omega_2$ to affect the amplitude and/or frequency modulation. This again results in noise suppression.

Figure 4:
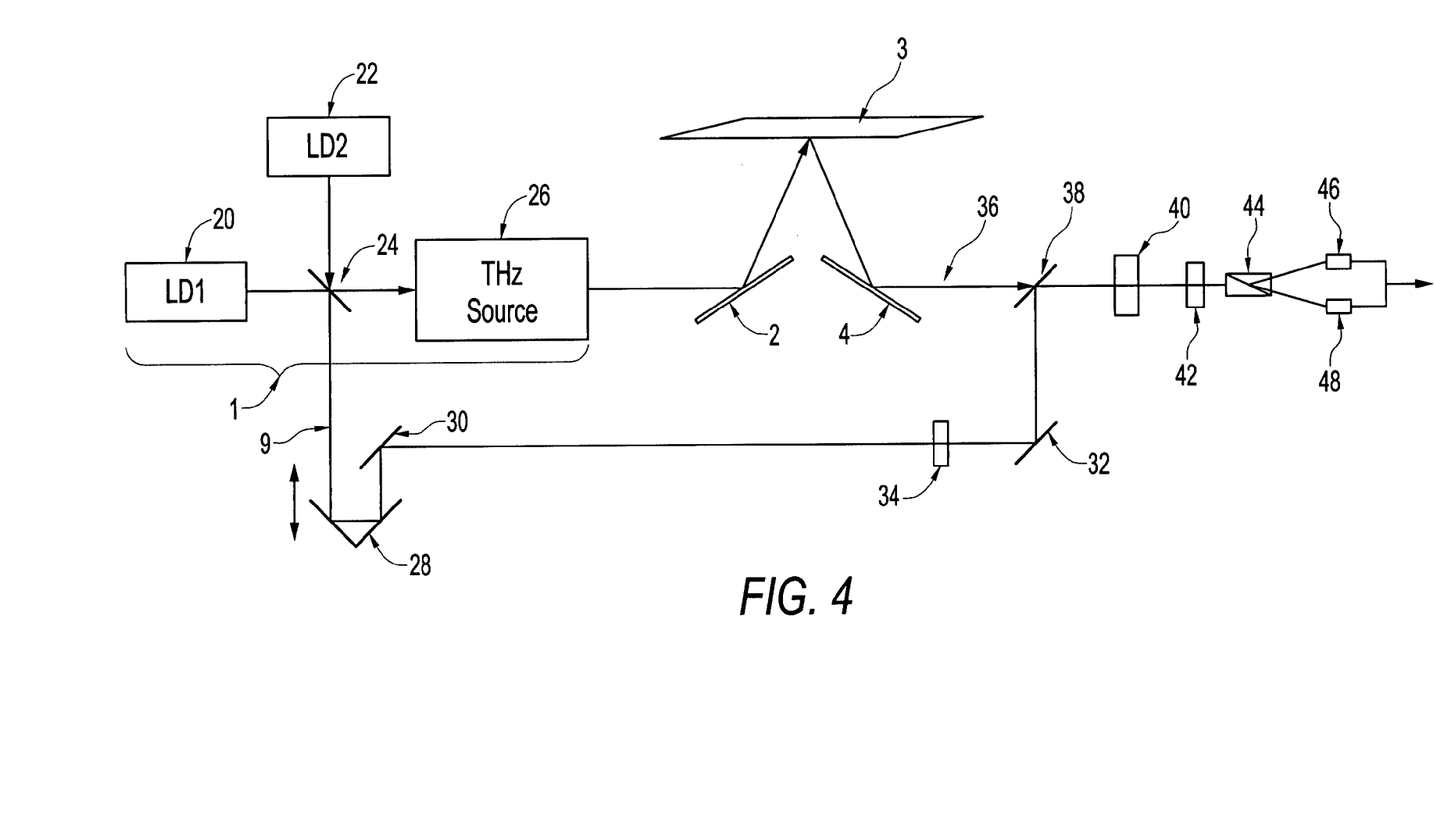

FIG. 4 shows a variation on the imaging system of FIG. 3. To avoid unnecessary repetition, like features will be denoted with like numerals. The generator 1, the sample and imaging apparatus and the optical delay line are identical to that described with reference to FIG. 3. Prior to the probe beam being reflected from mirror 32, the beam is passed through compensator 34 to ensure the probe beam is polarised parallel to the THz beam 36. After reflection from mirror 32, the probe beam 9 is reflected onto beam combiner 38. Beam combiner 38 will typically be a mirror to reflect the probe beam 9 and having an aperture which can transmit the THz radiation 36 coming from the sample 3.

The combined probe 9 and Terahertz 36 beams are then directed onto detection member 40. After the radiation has passed through the detection member, it is passed through a further number of optical and electrical elements.

Specifically, this FIG. 4 illustrates a possible detection mechanism which utilises the physical phenomenom known as the AC Pockels effect. The detector comprises a detection member 40. The transmitted THz radiation 36 from the sample 3 (FIG. 1) is detected by passing the 'probe beam' 9 through the detection member 9 with the THz beam 36. The THz beam 36 modulates the birefringence of the detection crystal 40 as the AC Pockels effect gives:

$$\chi_0 E_0 + \chi^{(2)} E_0 E_{THz} \Rightarrow n_o + \Delta n(E_{THz})$$

where $E_0$ and $E_{THz}$ are the electric fields of the visible and THz beams respectively, $n_0$ the visible refractive index, $\Delta n$ the change in refractive index induced by the THz electric field, and $\chi_0$ and $\chi^{(2)}$, the fundamental, and second order non-linear susceptibility, respectively.

Prior to entry into the detection member 40, the THz beam 36 and the probe beam 9 are polarised. In the situation where there is no THz beam, the probe beam passes unaffected through the detection crystal 40. It is then passed into quarter wave plate 42. This serves to circularly polarise the emitted radiation. The circularly polarised light is then fed through Wollaston prism 44 which divides the polarization of the light onto two orthogonal components. These two orthogonal components are then directed onto balanced photodiode assembly 46, 48. The balanced photodiode assembly comprises two photo diodes 46, 48 to respectively detect each of the orthogonal components from the Wollaston prism 44. The output of the photodiodes 46 and 48 are linked together such that the balanced photodiode assembly only outputs an electrical signal if there is a difference between the readings of the two photodiodes 46, 48.

Where there is a THz beam 36 this serves to make the radiation exiting the detection member 40 slightly elliptically polarised. This change in the polarization still remains after the radiation is passed through quarter waveplate 42. Extracting the orthogonal components of this radiation using prism 44 causes a different signal to be measured at the two photodiodes 46, 48 and hence balanced photodiode assembly outputs a signal corresponding to the strength of the THz field 36.

It should be noted that THz can be generated by using a THz source which does not use the method of varying an input radiation and instead directly outputs THz radiation in response to an input parameter such as a bias applied across the source. Typical sources are Gunn diodes, Molecular gas lasers, cascade lasers, backward wave oscillators and free electron lasers.

Figure 5:
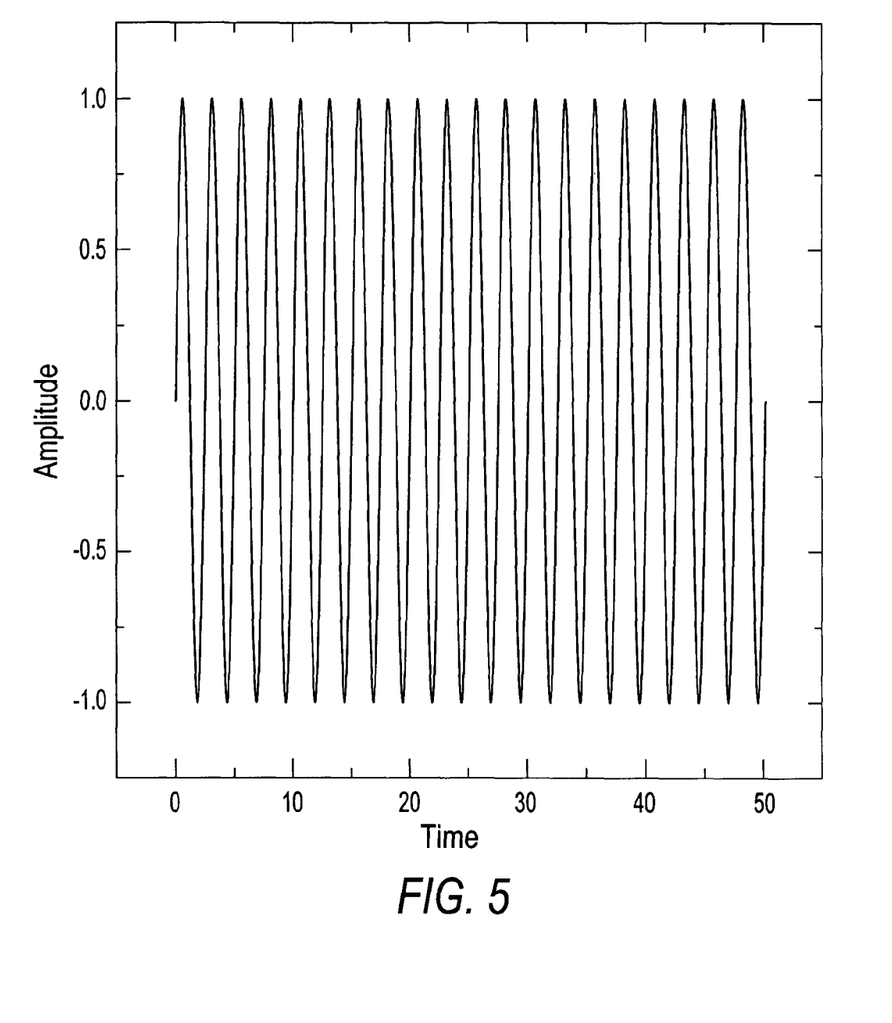
FIG. 5 shows a plot of detected signal versus time for a perfect coherent source

FIG. 5 shows an amplitude versus time plot for the idealized case that the emitter is a perfectly coherent source emitting at a single frequency. As can be seen in this case the detector records a sinusoidal function.

Figure 6:
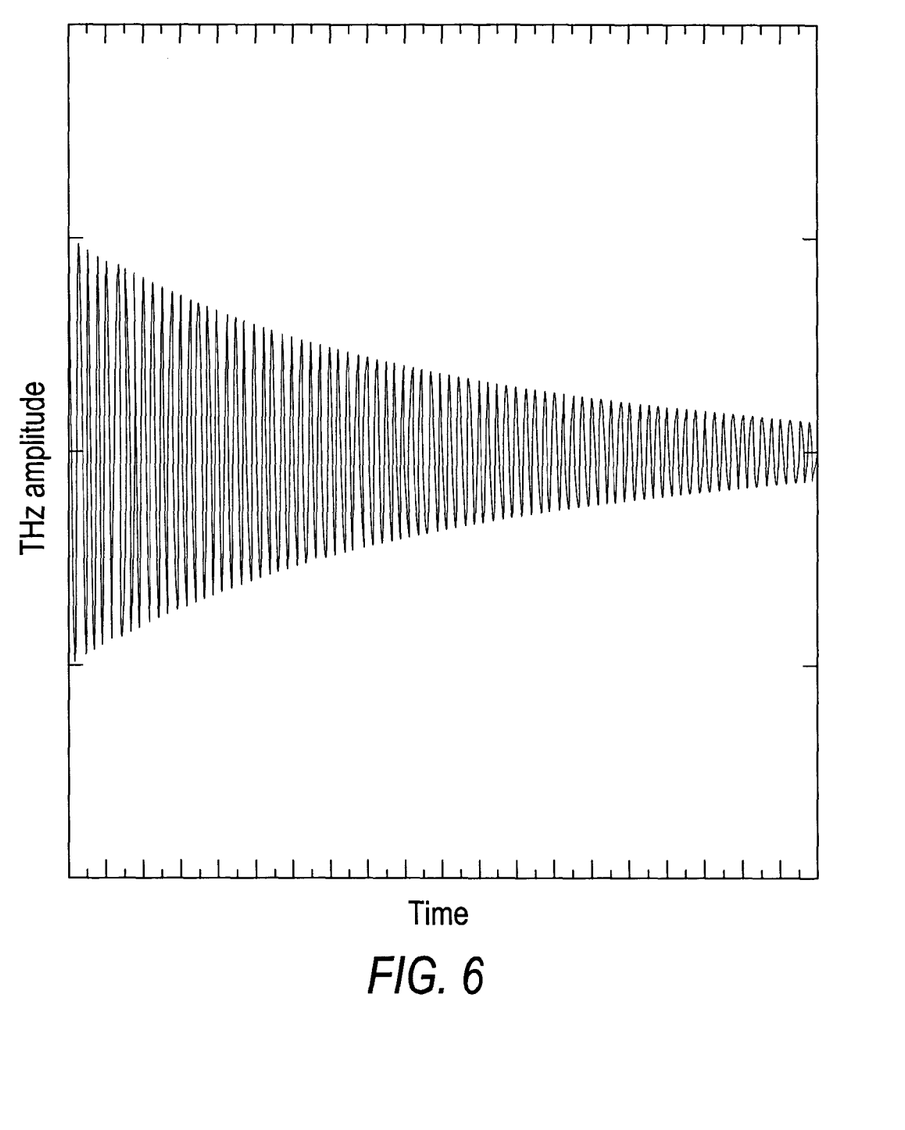
FIG. 6 shows detected signal versus time for a system with coherence length effects

In reality, however, the source will exhibit a defined coherence length and this will modify the detected beam until it resembles the schematic plot of amplitude versus time in FIG. 6. As can be seen the amplitude at each cycle decreases from an initial maximum value. The form of the decrease follows the well known correlation function, which generally resembles an exponential function.

The plot shown in FIG. 6 represents a reference signal and can be recorded if the sample is replaced with a perfectly reflecting mirror (for the case where the imaging system is set up to record reflections from a sample) or is absent (for the case where the imaging system is set up to record signals transmitted through the sample).

Figure 7:
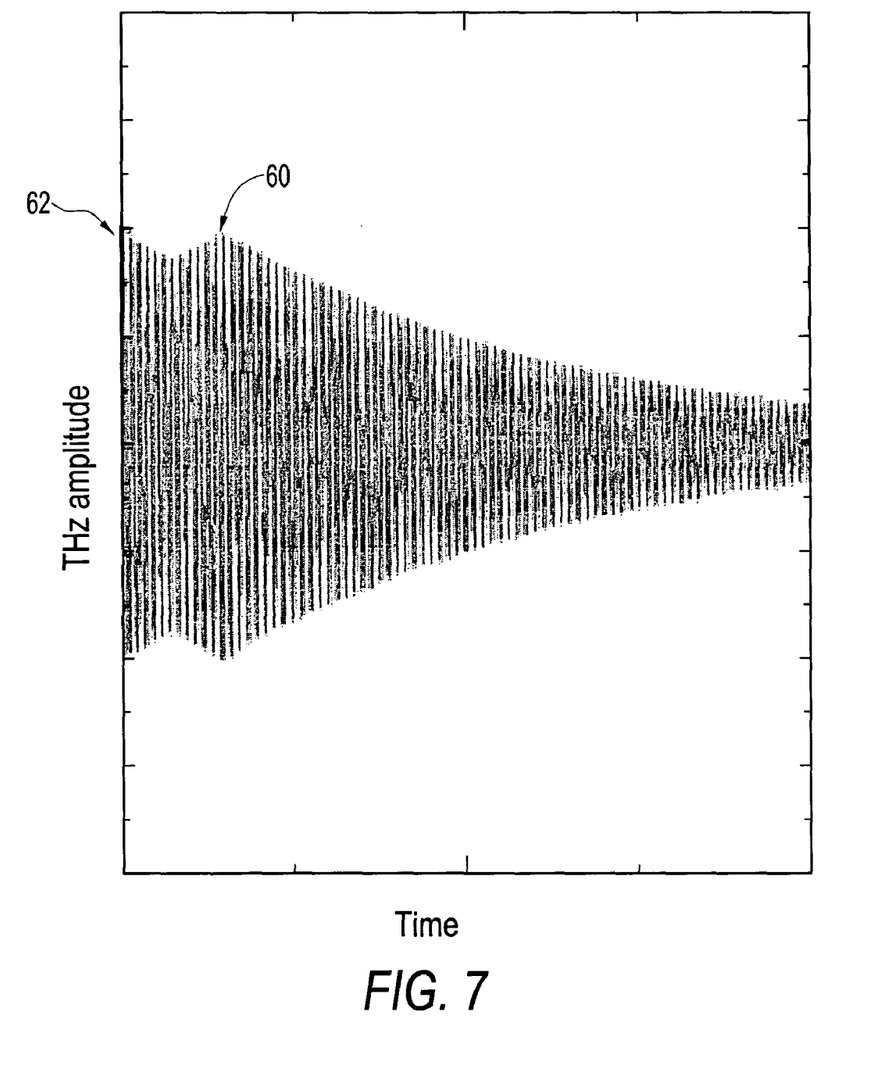
FIG. 7 shows the effect of signal retardation from imaging a sample

FIG. 7 shows schematically the detected beam that is recorded following reflection from a target sample (note: to simplify matters only a single reflection is shown). It can be seen that interaction with the sample has retarded the THz beam and introduced a phase shift into the detected signal compared to the reference signal 62 (i.e. a plot without the sample).

Varying the path length of the probe beam path allows the position of the maximum detected amplitudes of the reference signal and detected signal to be determined. A comparison of the position of the maximum detected amplitude then allows relative depth information within the sample to be determined.

It should be noted that previous continuous wave imaging techniques have only been able to determine a relative phase shift in the detected radiation. This would not allow relative or absolute depth information to be determined since it would be impossible to distinguish between phase shifts differing by $2\pi$, e.g. between a phase shift of $\frac{1}{2}\pi$ and $5\pi/2$.

A detailed analysis of the physics of this imaging system shows that the measured phase shift is actually the product of the path length change multiplied by the refractive index of the sample. Since changes in the refractive index throughout the sample are generally only of the order of one part in 100 the uncertainty in the depth measurements will be small.

Figure 8:
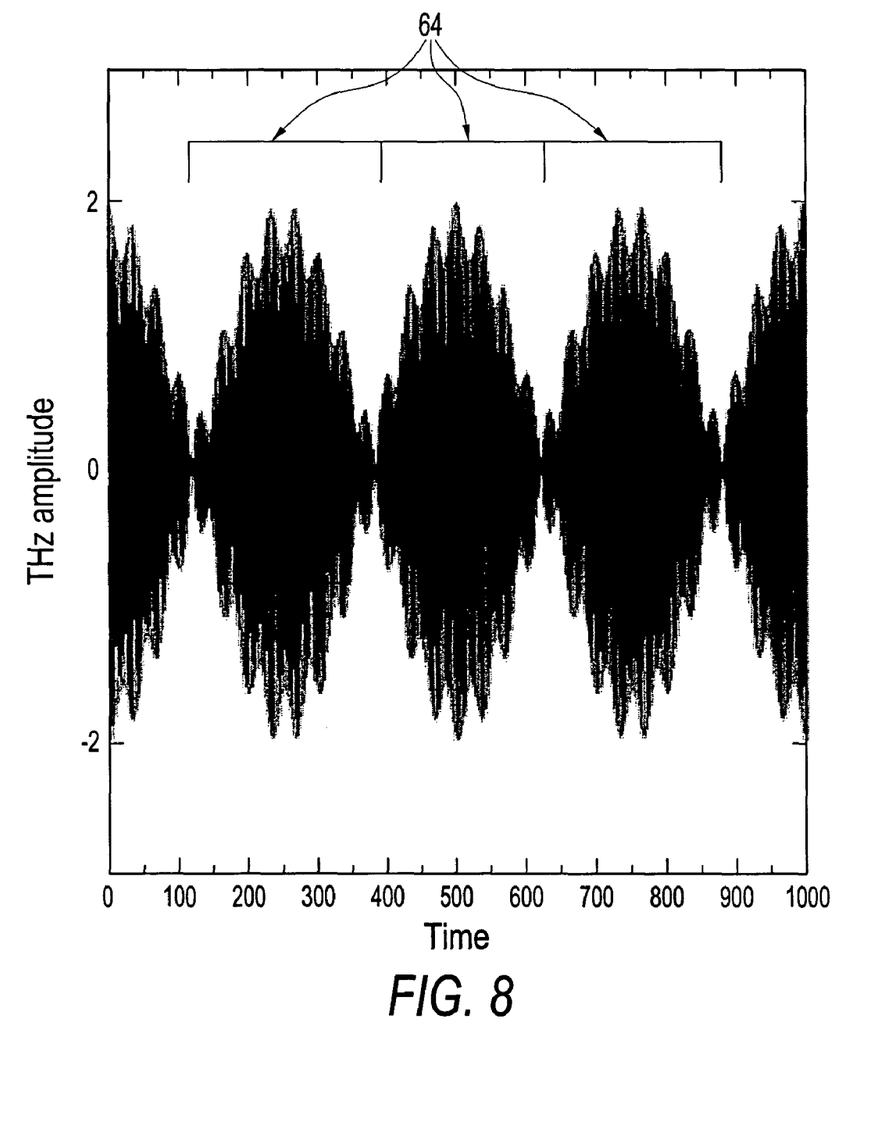
FIG. 8 shows a waveform which comprises a number of radiation frequencies

FIG. 8 shows a plot of a waveform constructed from three separate sinusoidal frequency elements, $\omega_1$, $\omega_2$, $\omega_3$. The waveform has been calculated using the figures $\omega_1 = 400$ GHz, $\omega_2 = 430$ GHz and $\omega_3 = 404$ GHz. The amplitudes of the three components were in the ratio $\omega_1 : \omega_2 : \omega_3$ of $1 : 0.1 : 0.8$. This combined waveform has a much more complex form than the waveform shown in FIG. 5. However, it can be seen that the waveform comprises a number of separate "wave-pulses" 64 each displaying similar characteristic structures.

Figure 9:
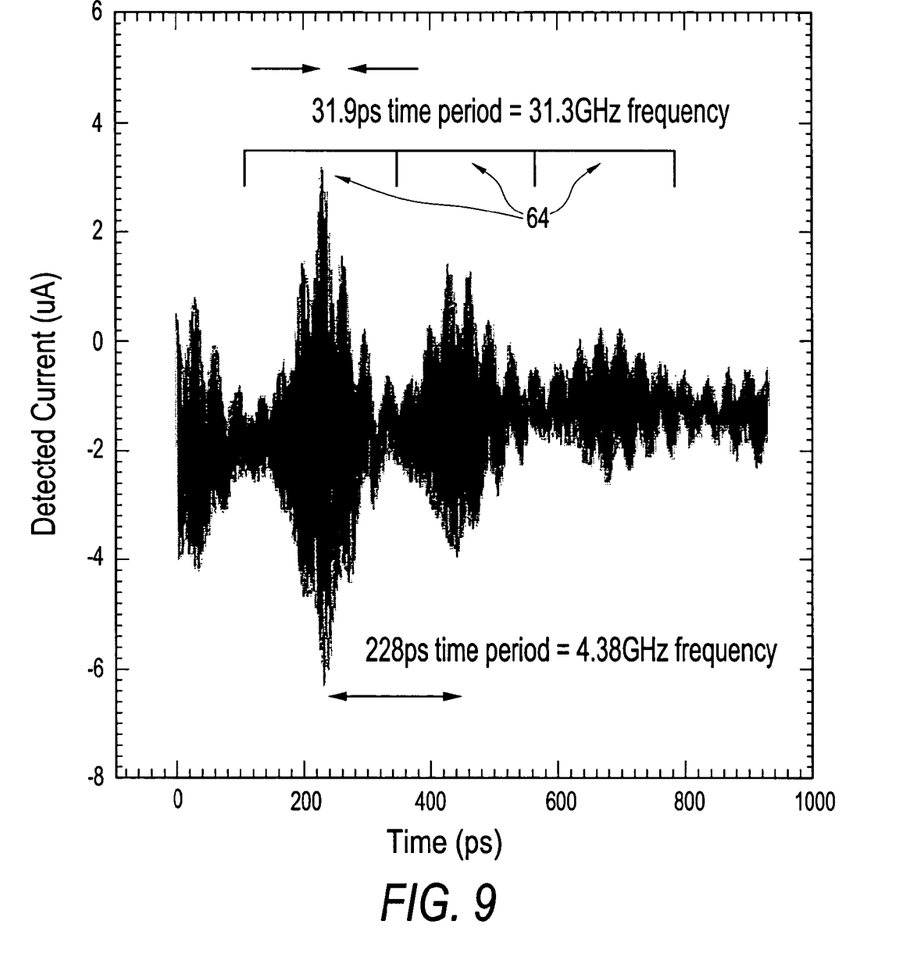
FIG. 9 shows the waveform of FIG. 9 in a system exhibiting coherence length effects (with no sample present)

FIG. 9 shows the measurement made at the detector in the absence of a sample when the waveform of FIG. 8 is generated by the emitter. The same characteristic structure as in FIG. 8 is evident as are the time periods for the oscillations. However, the effect of coherence within the system has reduced the amplitudes of the later pulses. The coherence effect has effectively encoded the wavepackets, so that the fundamental position of maximum amplitude can be uniquely identified.

The maximum detected amplitude is now obvious and compared to FIG. 7 it is now much easier to identify the position of this maximum amplitude.

Figure 10:
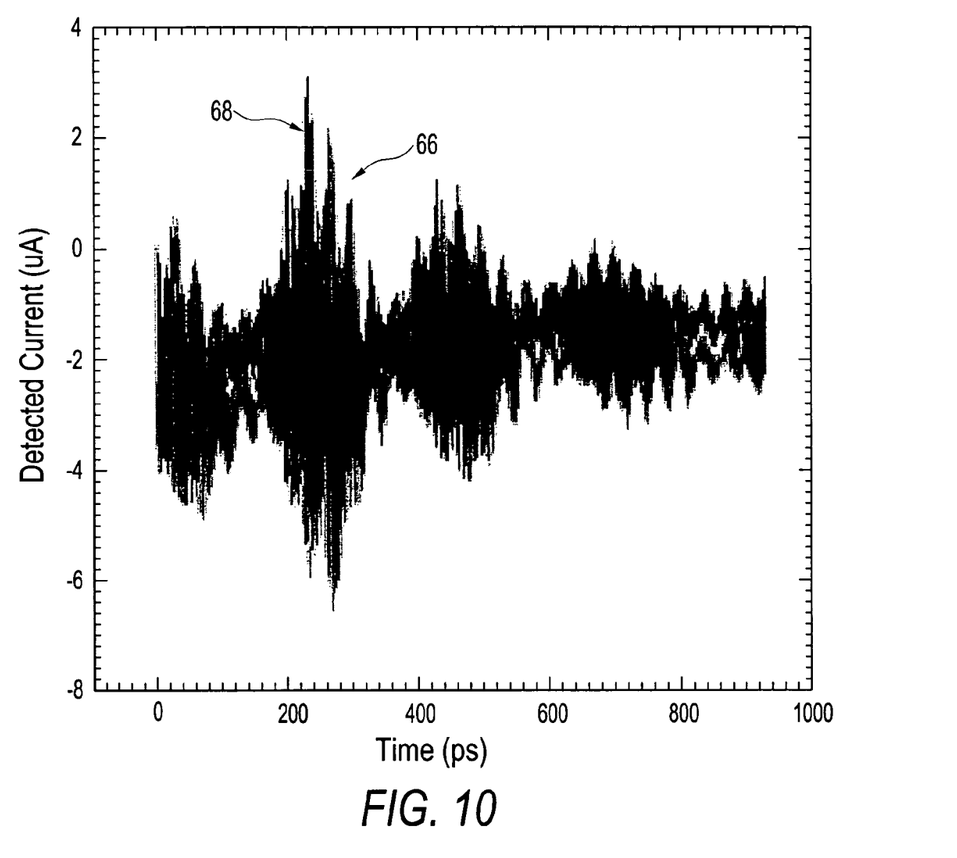
FIG. 10 shows the waveform of FIG. 9 in a system exhibiting coherence length effects (reference plot and sample present)

FIG. 10 shows the result when the emitted radiation beam of FIG. 8 is used to probe a sample. As in FIG. 7 the detected beam is retarded when compared to the reference beam (i.e. the plot shown in FIG. 9). However, in contrast to FIG. 7 it is now easier to identify the maximum amplitude position and therefore determine depth features within the sample.

Therefore, the effects of coherence within the system allow the depth information to be extracted from the sample and the "wave-packet" nature of the scanning beam allows that information to be extracted easily.

Figure 11:
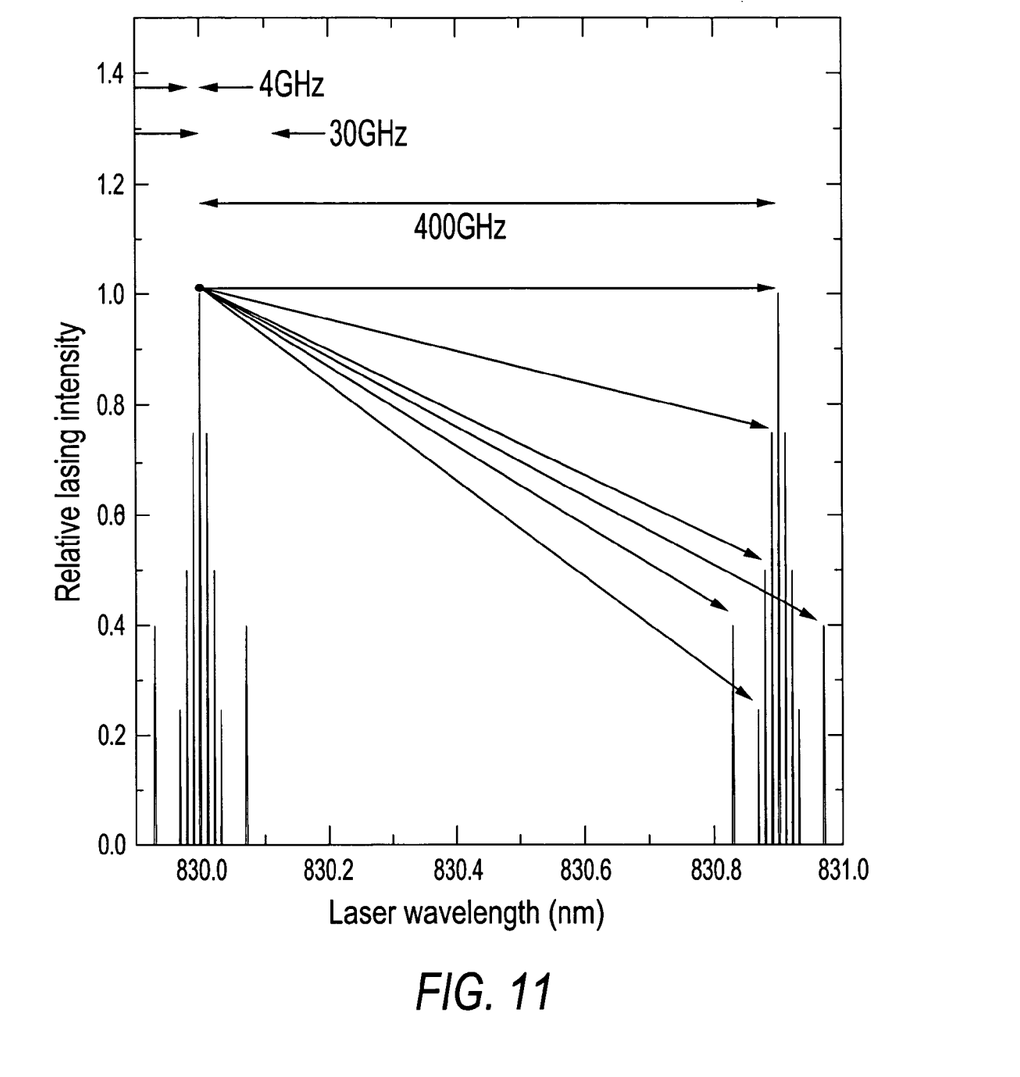
FIG. 11 shows the wavelength output of a typical diode laser

FIG. 11 shows the typical output from a diode laser. As can be seen the device lases at a variety of different wavelengths. When the diode laser is used to as the input beam for a frequency conversion member all of the combinations of lasing frequencies that excite the device will be mixed together (one set of combinations for just one of the lasing wavelengths is shown in the Figure). This results in a plurality of emitted THz frequencies which will form a complex waveform in a similar manner to that described with respect to FIG. 9.

The invention claimed is:
1. A method for imaging a sample, the method comprising:
 a) irradiating the surface of a sample with a source of coherent substantially monochromatic and substantially continuous radiation from a non-pulsed source with a frequency in the range 25 GHz to 100 THz, said radiation having at least one characteristic feature present in said radiation before said radiation irradiates the surface of the sample, said at least one characteristic feature being varied between successive cycles of radiation such that successive cycles of radiation from said non-pulsed source are distinguishable from one another;

b) detecting said radiation reflected from the sample;

c) providing and detecting a probe beam having a phase related to that of the radiation leaving the source; and d) analyzing the detected radiation for said at least one characteristic feature within the radiation and measuring any shift in the position of said at least one feature in the reflected radiation in order to derive structural information about the sample as a function of depth from the surface of the sample.

2. A method as claimed in claim 1, the method further comprising the step of detecting a reference signal wherein the at least one characteristic feature within the radiation upon interaction with the sample is compared to the equivalent at least one characteristic feature in the reference signal in order to determine any change in phase.

3. A method as claimed in claim 1, wherein the detected radiation comprises multiple reflected signals from the sample, the method further comprising determining the at least one characteristic feature within the radiation for each of the multiple signals and comparing such features in order to determine any changes in phase.

4. A method as claimed in claim 1, wherein the method further comprises the step of de-convolving the detected radiation to derive multiple reflected signals from the sample.

5. A method as claimed in claim 1, wherein the at least one characteristic feature is a feature inherent within the radiation.

6. A method as claimed in claim 1, wherein the optical path length of the probe beam between the source and the detector is varied in order to determine the phase dependent features of the detected radiation.

7. A method as claimed in claim 1, wherein the at least one characteristic feature determined from the radiation is the maximum detected amplitude of the radiation.

8. A method as claimed in claim 1, wherein the sample is irradiated with coherent substantially continuous radiation at least two different frequencies in the range 25 GHz to 100 THz.

9. A method as claimed in claim 8, wherein the peak amplitude of two or more of the at least two different frequencies are different.

10. A method according to claim 9, wherein the wave sources are diode lasers.

11. A method according to claim 8, wherein the input beams are provided by coherent continuous wave sources.

12. A method as claimed in claim 1, wherein the irradiating radiation is provided by at least one quantum cascade laser.

13. A method as claimed in claim 1, wherein the irradiating radiation is generated by a frequency conversion member which is configured to emit radiation of the desired frequency in response to irradiation by radiation from two or more input beams.

14. A method as claimed in claim 1, wherein the probe beam is obtained by dividing the beam of radiation which is used to irradiate the sample.

15. An apparatus for imaging a sample, the apparatus comprising:

a non-pulsed source for irradiating a sample with a beam of coherent substantially monochromatic and substantially continuous radiation having a frequency in the range 25 GHz to 100 THz, said radiation having at least one characteristic feature present in said radiation before said radiation irradiates the sample, said at least one characteristic feature being varied between successive cycles of radiation such that successive cycles of radiation from said non-pulsed source are distinguishable from one another;

a detector for detecting radiation reflected from the sample;

a probe beam having a phase related to that of the radiation leaving the source for detection by the detector; and means for analyzing the detected radiation for said at least one characteristic feature in the radiation and measuring any shift in the position of said at least one feature in the reflected radiation in order to derive structural information about the sample as a function of depth from the surface of the sample.

* * * * *